United States Patent
Ino

(10) Patent No.: US 8,989,605 B2
(45) Date of Patent: Mar. 24, 2015

(54) IMAGE FORMING APPARATUS

(71) Applicant: Canon Kabushiki Kaisha, Tokyo (JP)

(72) Inventor: Koichiro Ino, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 107 days.

(21) Appl. No.: 13/911,391

(22) Filed: Jun. 6, 2013

(65) Prior Publication Data
US 2013/0330091 A1 Dec. 12, 2013

(30) Foreign Application Priority Data

Jun. 8, 2012 (JP) .................. 2012-131298

(51) Int. Cl.
*G03G 15/00* (2006.01)
*G01N 21/27* (2006.01)
(52) U.S. Cl.
CPC ............. *G01N 21/27* (2013.01); *G03G 15/55* (2013.01); *G01N 21/276* (2013.01); *G03G 15/5062* (2013.01)
USPC .............................................. 399/9; 399/49
(58) Field of Classification Search
CPC ... G01N 21/27; G03G 15/55; G03G 15/5062; G03G 21/276

USPC ............ 356/402; 358/1.9, 474; 399/9–11, 49, 399/72
See application file for complete search history.

(56) References Cited

U.S. PATENT DOCUMENTS 7,433,088 B2 * 10/2008 Soeda ........................ 358/474
8,144,365 B2 * 3/2012 Kita et al. .................... 358/1.9

FOREIGN PATENT DOCUMENTS

JP 2004-086013 A 3/2004

* cited by examiner

*Primary Examiner* — Hoang Ngo
(74) *Attorney, Agent, or Firm* — Canon USA Inc. IP Division

(57) ABSTRACT

An image forming apparatus includes a plurality of white reference plates, a plurality of measurement units configured to be arranged in positions opposed to the respective plurality of white reference plates, irradiate the white reference plates with light, and measure reflected light from the white reference plates, and a determination unit configured to determine an abnormality of the plurality of white reference plates by using respective measurement results measured by the plurality of measurement units.

8 Claims, 11 Drawing Sheets

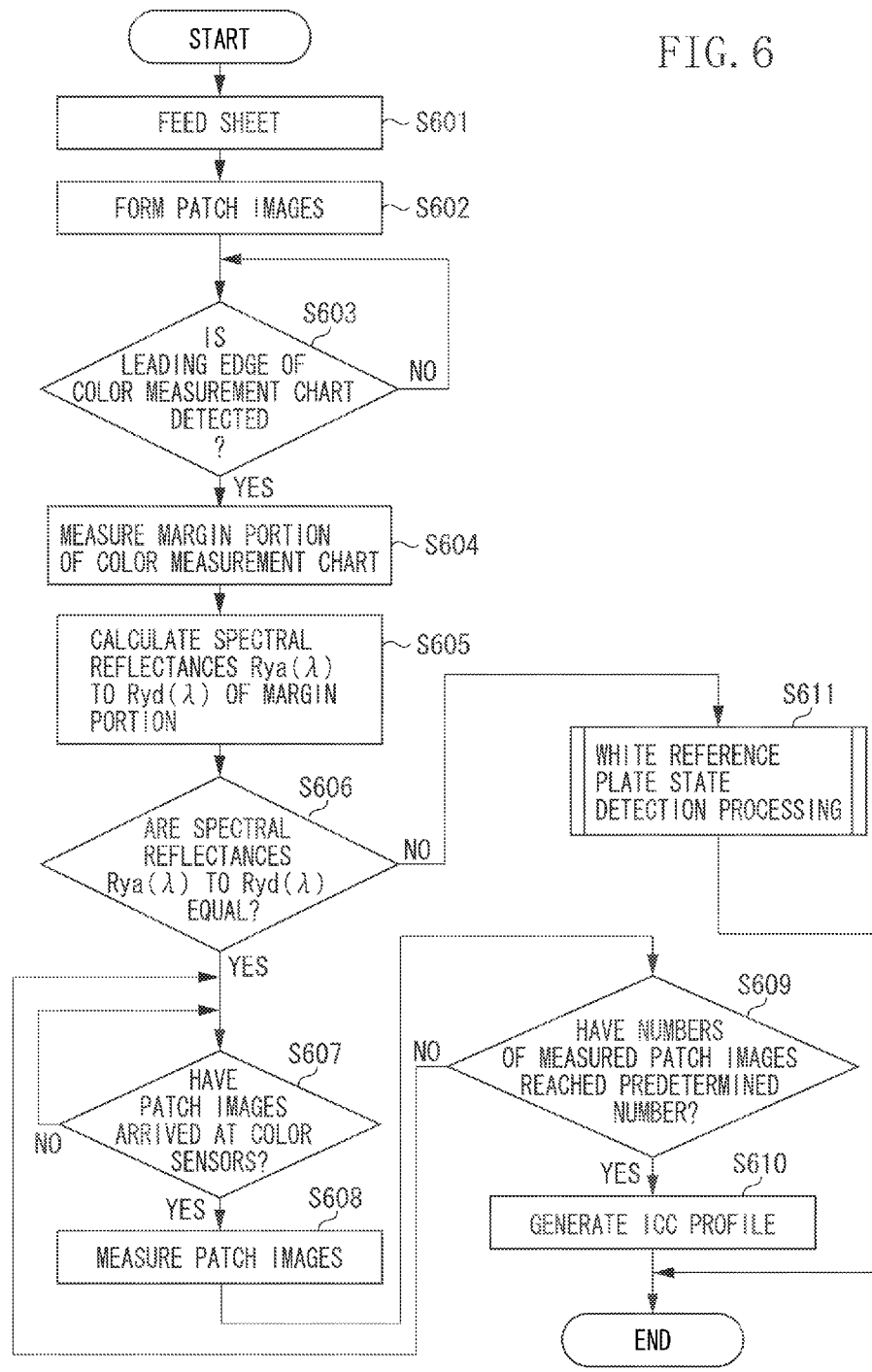

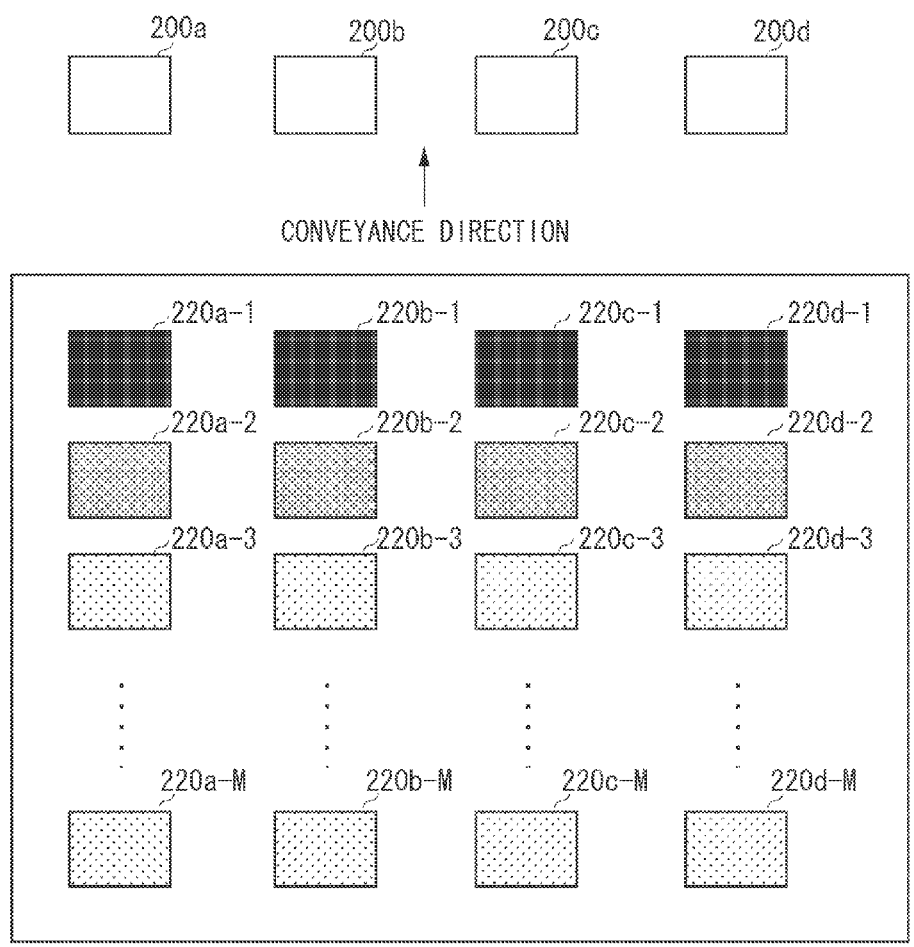

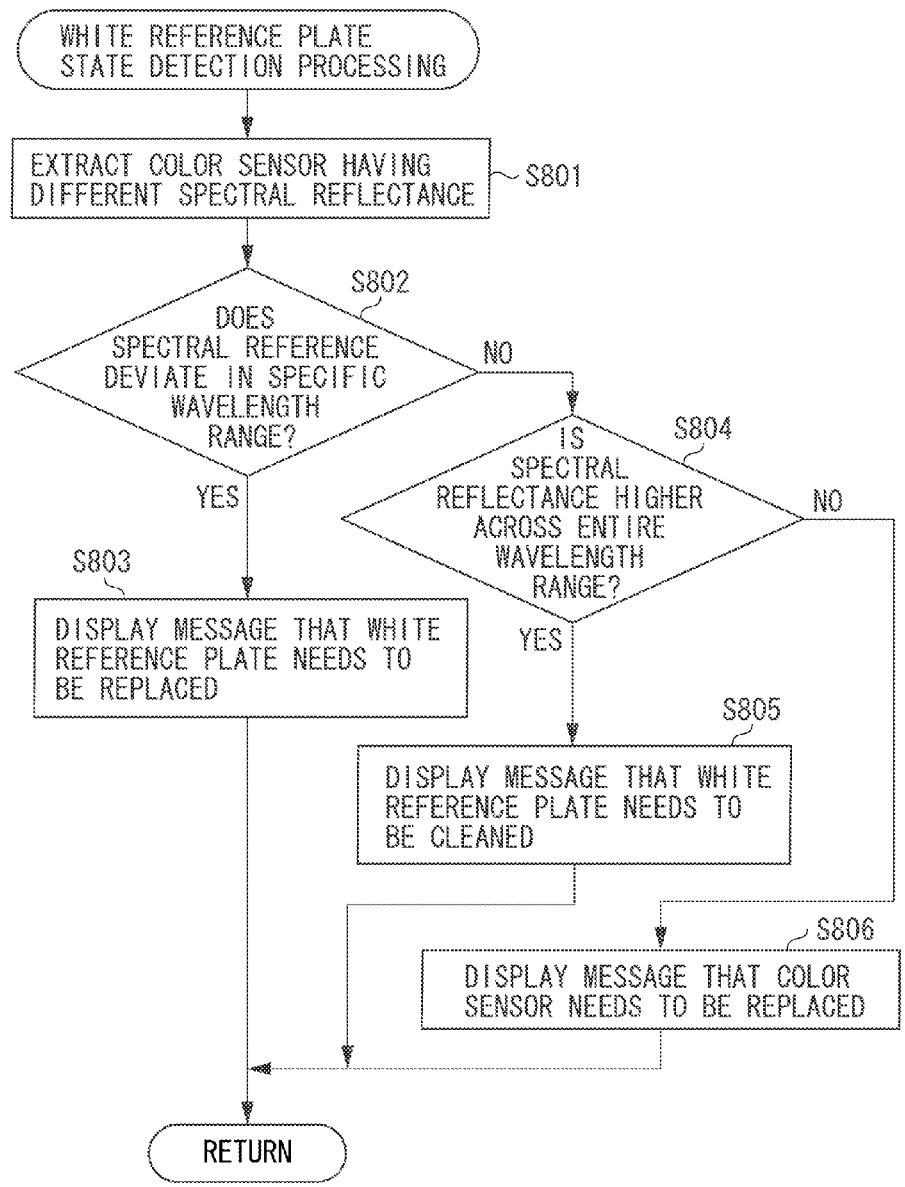

IMAGE FORMING APPARATUS

BACKGROUND OF THE INVENTION

1. Field of the Invention

The present disclosure generally relates to image forming and, more particularly, to an image forming apparatus having a function of measuring color of a measuring image.

2. Description of the Related Art

An image forming apparatus has image qualities such as granularity, in-plane uniformity, character quality, and color reproducibility (including color stability). With the proliferation of multicolor image forming apparatuses today, color reproducibility is sometimes said to be the most important image quality.

People have their empirically-grounded memories of expected colors (like human skin, blue sky, and metals), and exceeding an allowable range would give a sense of strangeness. Such colors are referred to as memory colors, whose reproducibility is being required more often when outputting photographs.

Office users are experiencing a sense of strangeness with document images as well as photographic images, in the presence of a color difference from a display monitor. Graphic arts users are pursuing color reproducibility of computer graphics (CG) images. Color reproducibility (including stability) demanded of image forming apparatuses by the above users is ever increasing.

To meet the users' demand for color reproducibility, for example, Japanese Patent Application Laid-Open No. 2004-086013 discusses an image forming apparatus that reads measurement images (patch images) formed on a sheet with a measurement unit (color sensor) arranged on a conveyance path of the sheet. According to the image forming apparatus, a process condition including the amount of exposure and a development bias can be feedback-controlled based on the reading result of the patch images by the color sensor, whereby a constant density, gradation, and tint can be reproduced.

The color detection accuracy of the color sensor discussed in Japanese Patent Application Laid-Open No. 2004-086013 deteriorates due to factors such as variations of the output of a light source due to a change in the ambient temperature. A white reference plate then may be arranged in a position opposed to the color sensor, so that the color sensor can measure the white reference plate and correct detected values of the color sensor.

Specifically, a spectral reflectance $R(\lambda)$ of a patch image can be determined by the following equation:

$$R(\lambda) = P(\lambda)/W(\lambda), \qquad \text{(Eq. 1)}$$

where $W(\lambda)$ is the reflected light amount from the white reference plate, and $P(\lambda)$ is the reflected light amount from the patch image.

The determination of the spectral reflectance $R(\lambda)$ by using the white reference plate has a problem in that the measured spectral reflectance $R(\lambda)$ can contain errors depending on a change in the state of the white reference plate such as a deterioration and stain of the white reference plate. For example, if the white reference plate undergoes a change because of tint variations of the white reference plate due to aged deterioration or the adhesion of a stain to the white reference plate, the original reflectance $W(\lambda)$ of the white reference plate is erroneously detected as $W'(\lambda)$. As a result, the spectral reflectance $R(\lambda)$ of the patch image is erroneously calculated as $R'(\lambda)$.

SUMMARY OF THE INVENTION

The present disclosure is directed to an image forming apparatus that can determine an abnormality of a white reference plate and can prevent a drop in the measurement accuracy of measurement images.

According to an aspect of the present disclosure, an image forming apparatus includes a plurality of white reference plates, a plurality of measurement units configured to be arranged in positions opposed to the respective plurality of white reference plates, irradiate the white reference plates with light, and measure reflected light from the white reference plates, and a determination unit configured to determine an abnormality of the plurality of white reference plates by using respective measurement results measured by the plurality of measurement units.

Further features and aspects of the present disclosure will become apparent from the following description of exemplary embodiments with reference to the attached drawings.

BRIEF DESCRIPTION OF THE DRAWINGS

FIG. 6 is a flowchart illustrating an operation for measuring patch images when performing multi-color correction processing.

FIG. 7 is a schematic diagram illustrating a color measurement chart.

FIG. 8 is a flowchart illustrating white reference plate state detection processing.

DESCRIPTION OF THE EMBODIMENTS

A first exemplary embodiment will be described.
Image Forming Apparatus

In the present exemplary embodiment, a method for solving the foregoing problem will be described by using an electrophotographic laser beam printer. While the electrophotography is employed as an example of an image forming method, an exemplary embodiment of the present disclosure may also be applied to inkjet printing and sublimation printing.

Figure 1:
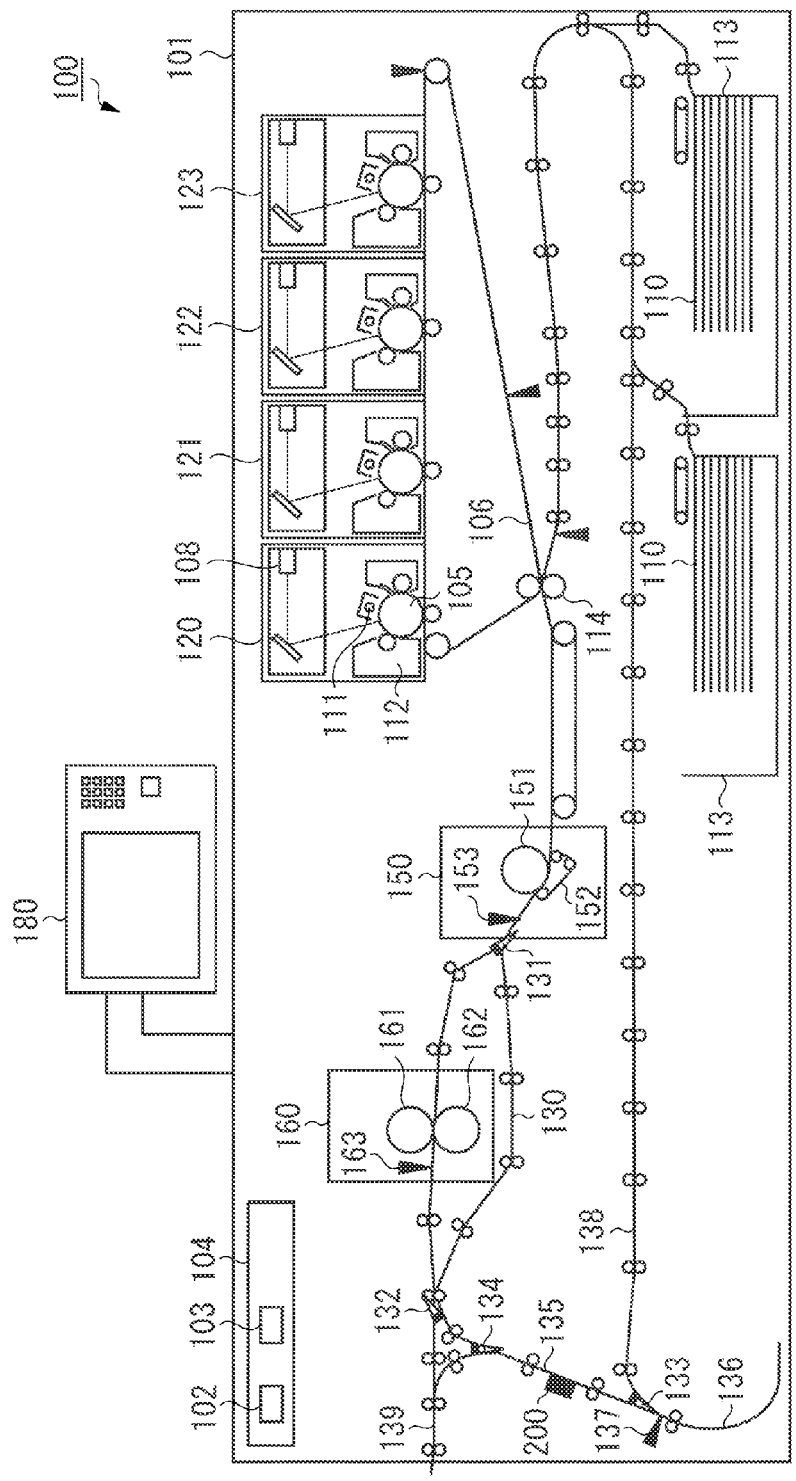
FIG. 1 is a sectional view illustrating a structure of an image forming apparatus 100.

FIG. 1 is a sectional view illustrating a structure of an image forming apparatus 100. The image forming apparatus 100 includes a housing 101. The housing 101 includes each mechanism for constituting an engine unit, and a control board accommodation unit 104. The control board accommodation unit 104 accommodates an engine control unit 102 and a printer controller 103. The engine control unit 102 performs control concerning each of printing processes by each of the mechanisms (such as sheet feeding processing).

As illustrated in FIG. 1, the engine unit includes four stations 120, 121, 122, and 123 corresponding to Y, M, C, and K. The stations 120, 121, 122, and 123 are image forming units for forming an image by transferring toner to a sheet 110. Y, M, C, and K are abbreviations of yellow, magenta, cyan, and black, respectively. The stations 120, 121, 122, and 123 include almost common components. Photosensitive drums 105 are a type of image bearing members. Primary charging devices 111 charge the photosensitive drums 105 with a uniform surface potential. Latent images are formed on the photosensitive drums 105 by laser light output from lasers 108. Developing units 112 develop the latent images by using color material (toner) to form toner images. The toner images (visible images) are transferred to an intermediate transfer member 106. A transfer roller 114 transfers the visible images formed on the intermediate transfer member 106 to a sheet 110 conveyed from a container 113.

A fixing processing mechanism according to the present exemplary embodiment includes a first fixing unit 150 and a second fixing unit 160 which apply heat and pressure to the toner images transferred to the sheet 110 and thereby fix the toner images to the sheet 110. The first fixing device 150 includes a fixing roller 151 for applying heat to the sheet 110, a pressure belt 152 for pressing the sheet 110 against the fixing roller 150, and a first post-fixing sensor 153 which detects completion of fixing. The fixing roller 151 is a hollow roller and includes a heater inside.

The second fixing device 160 is arranged downstream from the first fixing device 150 in a conveyance direction of the sheet 110. The second fixing device 160 gives gloss to the toner image on the sheet 110, fixed by the first fixing device 150, and/or ensures fixability. Like the first fixing device 150, the second fixing device 160 includes a fixing roller 161, a pressure roller 162, and a second post-fixing sensor 163. Some types of sheets 110 need not be subjected to the second fixing device 160. Such sheets 110 pass through a conveyance path 130 to bypass the second fixing device 160 for the sake of reducing energy consumption.

For example, if a setting is made to give more gloss to the image on the sheet 110 or if the sheet 110 needs a greater amount of heat for fixing like thick paper, the sheet 110 passed through the first fixing device 150 is conveyed to the second fixing device 160. On the other hand, if the sheet 110 is plain paper or thin paper and there is no setting to give more gloss, the sheet 110 is conveyed to the conveyance path 130 to detour around the second fixing device 160. Whether to convey the sheet 110 to the second fixing device 160 or convey the sheet 110, detouring around the second fixing device 160 is controlled by switching a switching member 131.

A switching member 132 is a guide member that guides the sheet 110 to either a conveyance path 135 or an external discharge path 139. A leading edge of the sheet 110 guided to the conveyance path 135 passes through a sensor 137 and is conveyed to a reversing unit 136. The conveyance direction of the sheet 110 is switched when the sensor 137 detects a trailing edge of the sheet 110. A switching member 133 is a guide member that guides the sheet 110 to either a conveyance path 138 for two-sided image formation or the conveyance path 135.

Color sensors 200 for detecting measurement images (hereinafter, patch images) on the sheet 110 are arranged on the conveyance path 135. As illustrated in FIG. 7, four color sensors 200a to 200d are juxtaposed in a direction orthogonal to the conveyance direction of the sheet 110, whereby four columns of patch images can be detected. When an instruction for color detection is given from an operation unit 180, the engine control unit 102 performs a density adjustment, a gradation adjustment, and a multi-color adjustment.

A switching member 134 is a guide member that guides the sheet 110 to the external discharge path 139. The sheet 110 conveyed through the discharge path 139 is discharged out of the image forming apparatus 100.

Color Sensors

Figure 2:
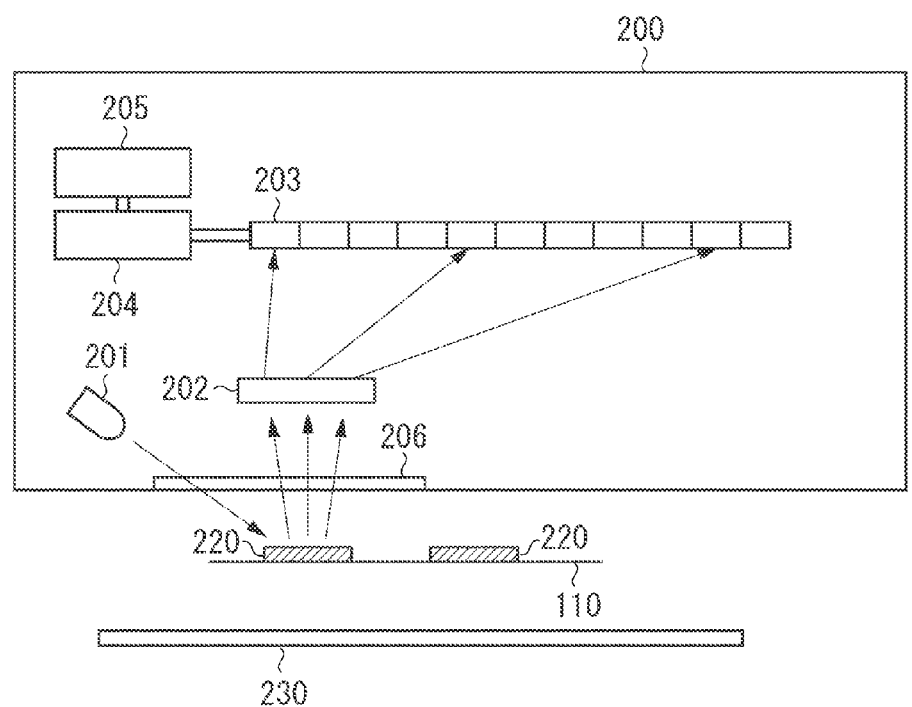
FIG. 2 is a diagram illustrating a structure of a color sensor 200.

FIG. 2 is a diagram illustrating a structure of the color sensors 200. A color sensor 200 includes a white LED 201, a diffraction grating 202, a line sensor 203, a calculation unit 204, and a memory 205. The white LED 201 is a light emitting element which irradiates a patch image 220 on the sheet 110 with light. The light reflected from the patch image 220 passes through a sensor window 206 made of a transparent member.

The diffraction grating 202 disperses the light reflected from the patch image 220 by wavelength. The line sensor 203 is a light detection device including n light receiving elements for detecting the light dispersed by wavelength by the diffraction grating 202. The calculation unit 204 performs various calculations based on light intensity values of respective pixels detected by the line sensor 203.

The memory 205 saves various types of data to be used by the calculation unit 204. For example, the calculation unit 204 includes a spectral calculation unit that performs a spectral calculation based on light intensity values, and a Lab calculation unit that calculates Lab values. The color sensor 200 may further include a lens that condenses the light emitted from the white LED 201 upon the patch image 220 on the sheet 110 and/or condenses the light reflected from the patch image 220 upon the diffraction grading 202.

A white reference plate 230 is detachably attached to a position opposed to the sensor window 206 of the color sensor 200. In FIG. 2, the white reference plate 230 is illustrated as being away from the sensor window 206 (detached state). In an actual measurement operation of the white reference plate 230, the white reference plate 230 is put close to the sensor window 206 (attached state). In other words, when measuring the white reference plate 230, the color sensor 200 measures reflected light from the white reference plate 230 with the white reference plate 230 in the attached state. Detection values of the color sensor 200 are corrected based on such reflected light.

Profile

For multi-color correction processing, the image forming apparatus 100 generates a profile from detection results of the patch images 220 including multi-colors, and converts an input image into an output image by using the profile.

The patch images 220 including multi-colors are formed by changing half dot area ratios of the four colors C, M, Y, and K in three levels (0%, 50%, and 100%) each. The patch images 220 are formed for all combinations of the halftone dot area ratios for each color. As illustrated in FIG. 7, the patch images 220 are formed in four columns to be read by the respective color sensors 200a to 200d.

An International Color Consortium (ICC) profile, which has been commercially prevalent in recent years, is used here as a profile for excellent color reproducibility. However, the application of an exemplary embodiment of the present invention is not limited to an ICC profile. An exemplary embodiment of the present invention may be applied to a color rendering dictionary (CRD) which is employed in Post-Script level 2 and above, advocated by Adobe Systems Incorporated, and a color separation table in Photoshop (registered trademark).

A user operates the operation unit 180 to issue an instruction for color profile generation processing when a customer engineer performs component replacement, before a job that requires high color matching precision, and when the tint of a final output matter needs to be checked in a design planning phase.

Figure 3:
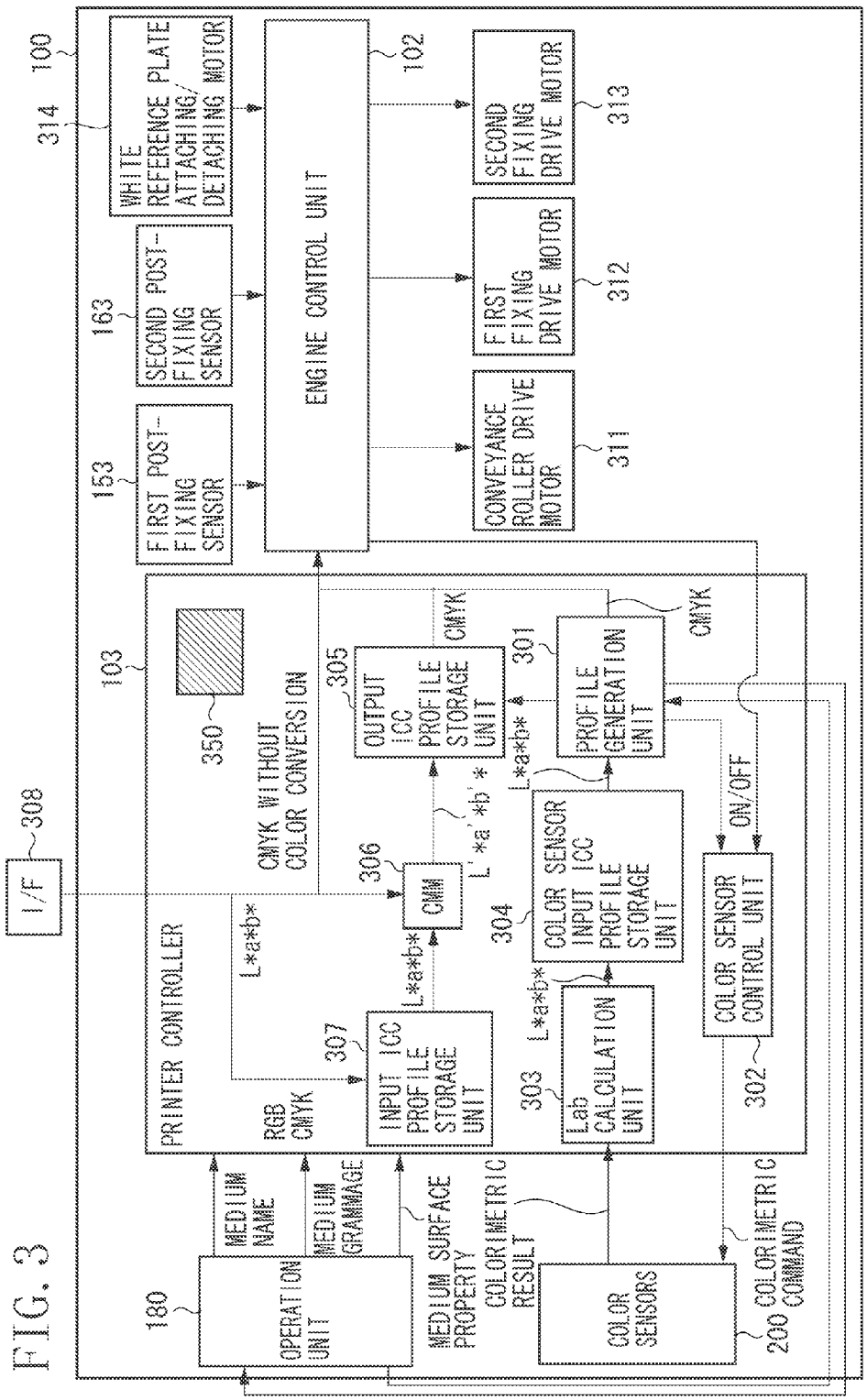
FIG. 3 is a block diagram illustrating a system configuration of the image forming apparatus 100.

FIG. 3 is a block diagram illustrating the printer controller 103 which performs the color profile generation processing. The printer controller 103 includes a central processing unit (CPU). The printer controller 103 reads a program for executing a flowchart to be described below from a storage unit 350 and executes the program. For easy understanding of processing performed by the printer controller 103, FIG. 3 illustrates the interior of the printer controller 103 in blocks.

When the operation unit 180 accepts an instruction for profile generation, a profile generation unit 301 outputs a CMYK color chart 210 to the engine control unit 102 without using a profile. The CMYK color chart 210 is an International Organization for Standardization (ISO) 12642 test form. The profile generation unit 301 sends a measurement instruction to a color sensor control unit 302. The engine control unit 102 controls the image forming apparatus 100 to perform processes such as charging, exposure, development, transfer, and fixing. As a result, the ISO 12642 test form is formed on a sheet 110. The color sensor control unit 302 controls the color sensors 200 to measure the ISO 12642 test form. The color sensors 200 output spectral reflectance data, which is measured value, to a Lab calculation unit 303 of the printer controller 103. The Lab calculation unit 303 converts the spectral reflectance data into L*a*b* data and outputs the L*a*b* data to the profile generation unit 301. The L*a*b* data is transmitted via a color sensor input ICC profile storage unit 304. The Lab calculation unit 303 may convert the spectral reflectance data into an International Commission on Illumination (CIE) 1931 XYZ color system which is a device-independent color space signal.

The profile generation unit 301 generates an output ICC profile from a relationship between the CMYK color signal to the engine control unit 102 and the L*a*b* data input from the Lab calculation unit 303. The profile generation unit 301 stores the generated output ICC profile into an output ICC profile storage unit 305.

The ISO 12642 test form includes patches of a CMYK color signal that cover a color reproduction range a typical copying machine can output. The profile generation unit 301 then generates a color conversion table from a relationship between the respective color signal values and measured L*a*b* values. In other words, the profile generation unit 310 generates a CMYK-to-Lab conversion table. Based on the CMYK-to-Lab conversion table, the profile generation unit 301 generates an inverse conversion table.

When the profile generation unit 301 accepts a profile generation command from a host computer via an interface (I/F) 308, the profile generation unit 301 outputs the generated output ICC profile to the host computer via the I/F 308. The host computer can perform a color conversion corresponding to the ICC profile on an application program.

A first fixing driving motor 312 is a motor for driving the first fixing device 150. A second fixing driving motor 313 is a motor for driving the second fixing device 160. The first and second fixing drive motors 312 and 313 are controlled by the engine control unit 102. The engine control unit 102 further controls a white reference plate attaching/detaching motor 314 for attaching and detaching the white reference plates 230 to/from the sensor windows 206 of the color sensors 200.

Color Conversion Processing

For color conversion for an ordinary color output, an image signal assuming RGB signal value or Japan Color or other standard printing CMYK signal value input from a scanner unit via the I/F 308 is sent to an input ICC profile storage unit 307 intended for external input. According to the image signal input from the I/F 308, the input ICC profile storage unit 307 performs an RGB-to-L*a*b* or CMYK-to-L*a*b* conversion. The input ICC profile storage unit 307 stores an input ICC profile including a plurality of lookup tables (LUTs).

Examples of the LUTs include a one-dimensional LUT for controlling a gamma value of the input signal, a multi-color LUT called direct mapping, and a one-dimensional LUT for controlling the gamma value of generated conversion data. Using such LUTs, the input ICC profile storage unit 307 converts the input image signal from the device-dependent color space into device-independent L*a*b* data.

The input ICC profile storage unit 307 inputs the image signal converted into L*a*b* coordinates to a color management module (CMM) 306. The CMM 306 performs various color conversions. For example, the CMM 306 performs a gamut conversion to map mismatches between a reading color space of the scanner unit serving as an input device and an output color reproduction range of the image forming apparatus 100 serving as an output device. The CMM 306 also performs a color conversion for adjusting a mismatch between a light source type at the time of input and a light source type with which an output product is observed (referred to as a mismatch between color temperature settings).

The CMM 306 thus converts the L*a*b* data into L'*a'*b'* data, and outputs the L'*a'*b'* data to the output ICC profile storage unit 305. The output ICC profile storage unit 305 contains the profile generated by measurement. The output ICC profile storage unit 305 performs color conversion by using the newly created ICC profile to convert the L'*a'*b'* data into a CMYK signal dependent on the output device, and outputs the CMYK signal to the engine control unit 102.

Figure 4:
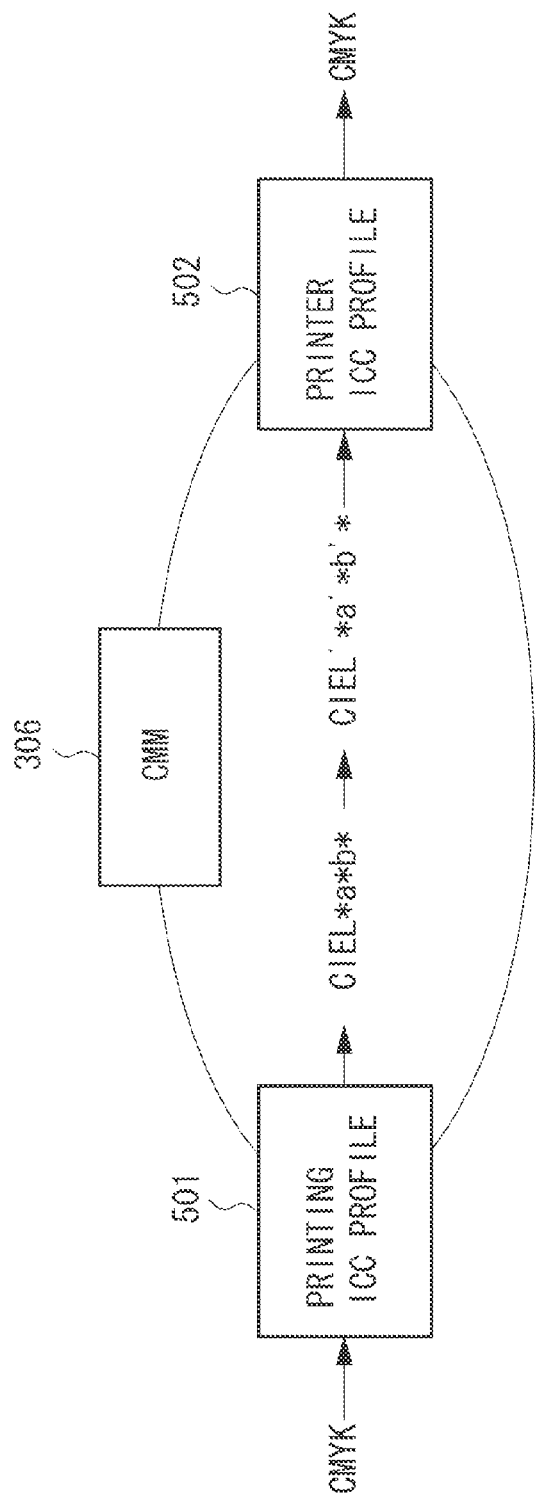
FIG. 4 is a schematic diagram illustrating a color management environment.

In FIG. 3, the CMM 306 is separated from the input ICC profile storage unit 307 and the output ICC profile storage unit 305. However, as illustrated in FIG. 4, the CMM 306 is a module that governs the color management. In fact, the CMM 306 performs a color conversion by using an input profile (printing ICC profile 501) and an output profile (printer ICC profile 502).

Up to this point, basic operations of the measurement of spectral reflectances by the color sensors 200, the calculation of color values (L*a*b*), the generation of an ICC profile, and the color conversion processing have been described. Now, a method for detecting a state of the white reference plates 230 by measuring the spectral reflectance of a margin portion of a sheet 110 by the plurality of color sensors 200a to 200d will be described in detail below.

Measuring Operation of White Reference Plate

Figure 5:
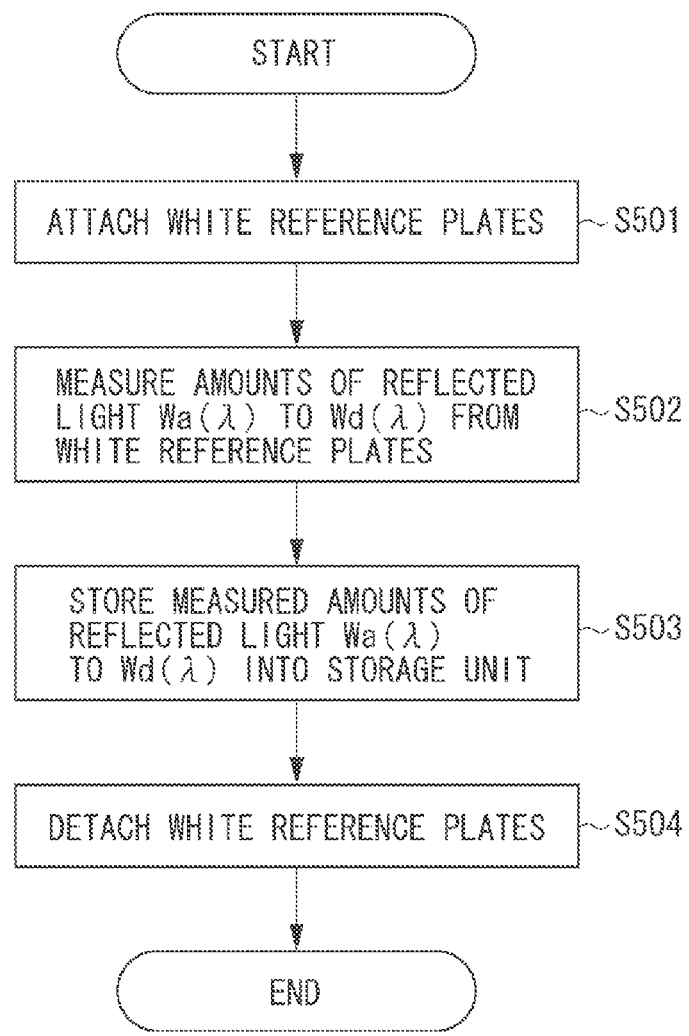
FIG. 5 is a flowchart illustrating an operation for measuring white reference plates 230.

FIG. 5 is a flowchart illustrating an operation for measuring the white reference plates 230.

This flowchart is executed by the printer controller 103. The control of the present flowchart is executed at timing before measurement of the patch images 220 and after a previous job ends and there is no sheet between the white reference plate 230a and the color sensor 200a. The engine control unit 102 controls the image forming apparatus 100 according to instructions from the printer controller 103.

In step S501, the printer controller 103 drives the white reference plate attaching/detaching motor 314 to attach the white reference plates 230a to 230d to the sensor windows 206 of the color sensors 200a to 200d in respective opposed positions. In step S502, after the completion of the attaching operation, the printer controller 103 measures the reflected light amounts Wa(λ) to Wd(λ) from the white reference plates 230 at each wavelength.

In step S503, the printer controller 103 stores the measured reflected light amounts Wa(λ) to Wd(λ) into the storage unit 350. In step S504, the printer controller 103 drives the white reference plate attaching/detaching motor 314 to detach the white reference plates 230a to 230d from the sensor windows 206 of the color sensors 200a to 200d, and ends the processing of the flowchart.

FIG. 6 is a flowchart illustrating an operation for measuring the patch images 220 when performing multi-color correction processing.

This flowchart is executed by the printer controller 103. The engine control unit 102 controls the image forming apparatus 100 according to instructions from the printer controller 103.

In step S601, the printer controller 103 makes the image forming apparatus 100 feed a sheet 110 from the container 113. In step S602, the printer controller 103 forms the patch images 220 for multi-color correction processing on the sheet 110 to generate a color measurement chart. As illustrated in FIG. 7, the color measurement chart includes a plurality (M) of patch images 220 which are arranged in positions opposed to each of the color sensors 200a to 200d at regular distances.

In step S603, the color measurement chart is conveyed to the color sensors 200, and the color sensors 200 detects a leading edge of the color measurement chart. If the leading edge is detected (YES in step S603), then in step S604, after predetermined timing, the printer controller 103 makes the color sensors 200a to 200d measure a margin portion at the leading edge of the color measurement chart.

In step S605, the printer controller 103 calculates the reflected light amounts Ya(λ) to Yd(λ) from the margin portion at each wavelength, corresponding to the color sensors 200a to 200d, respectively. The printer controller 103 further calculates spectral reflectances Rya(λ) to Ryd(λ) of the margin portion based on the foregoing equation (Eq. 1) by using the calculated reflected light amounts Ya(λ) to Yd(λ) and the reflected light amounts Wa(u) to Wd(λ) stored in the storage unit 305 in step S503.

In step S606, the printer controller 103 compares the spectral reflectances Rya(λ), Ryb(λ), Ryc(λ), and Ryd(λ) across the entire wavelength range to determine whether the spectral reflectances Rya(λ), Ryb(λ), Ryc(λ), and Ryd(λ) are equal. If the spectral reflectances Rya(λ), Ryb(λ), Ryc(λ), and Ryd(λ) are determined to be equal (YES in step S606), then in step S607, the printer controller 103 waits until the patch images 220 arrive at the color sensors 200.

First patch images 220a-1 to 220d-1 to be measured have a high density. The printer controller 103 determines the arrival of the patch images 220 in response to a change of the output values of the color sensors 200a to 200d from the values of a blank portion of the color measurement chart. If the patch images 220 arrive at the color sensors 200 (YES in step S607), then in step S608, the printer controller 103 measures the patch images 220 by using the color sensors 200.

In step S609, the printer controller 103 determines whether the numbers of patch images 200 measured by the respective color sensors 200a to 200d have reached a predetermined number (M). If the numbers of patch images 200 have not reached the predetermined number (M) (NO in step S609), the printer controller 103 returns to the foregoing step S607.

If the numbers of patch images 200 have reached the predetermined number (M) (YES in step S609), then in step S610, the printer controller 103 determines the spectral reflectances of the patch images 200 measured in step S608, and generates the foregoing ICC profile based on the spectral reflectances. The printer controller 103 sets the ICC profile serving as an image forming condition to the output ICC profile storage unit 305 based on the measurements of the color sensors 200a to 200d. The printer controller 103 then ends the flowchart.

In the foregoing step S604, the color sensors 200 measure the margin portion of the same sheet. The spectral reflectances Rya(λ) to Ryd(λ) of the margin portion measured by the plurality of color sensors 200 are therefore supposed to be equal. If not, it is considered that some abnormality occurs. If, in step S606, the spectral reflectances Rya(λ), Ryb(λ), Ryc (λ), and Ryd(λ) are determined not to be equal (NO in step S606), then in step S611, the printer controller 103 performs white reference plate state detection processing.

White Reference Plate State Detection Processing

FIG. 8 is a flowchart illustrating the white reference plate state detection processing.

This flowchart is executed by the printer controller 103. The engine control unit 102 controls the image forming apparatus 100 according to instructions from the printer controller 103.

In step S801, the printer controller 103 refers to the spectral reflectances Rya(λ) to Ryd(λ) of the margin portion detected by the color sensors 200a to 200d, and extracts a color sensor 200x whose spectral reflectance is different from those of the other color sensors 200.

For example, the printer controller 103 extracts such a color sensor 200x by determining how far a spectral reflectance deviate from an average of the spectral reflectances Rya(λ) to Ryd(λ) of the color sensors 200a to 200d. More specifically, the printer controller 103 calculates an average Ry_ave(λ) of the spectral reflectances Rya(λ) to Ryd(λ) of the margin portion detected by the color sensors 200a to 200d, and compares the average Ry_ave(λ) with each of the spectral reflectances Rya(λ) to Ryd(λ). The extraction method is not limited thereto, and other extraction methods may be used.

In step S802, the printer controller 103 compares the spectral reflectance Ryx(λ) of the color sensor 200x with the average Ry_ave(λ), and determines whether the spectral reflectance Ryx(λ) deviates in a specific wavelength range. If the spectral reflectance Ryx(λ) deviates in a specific wavelength range (YES in step S802), the white reference plate 230 may be considered to be deteriorated.

The white reference plates 230 desirably have high light resistance for suppressing aged deterioration, and high strength in view of the attaching and detaching operations. For example, the white reference plates 230 are made of ceramic-processed aluminum oxide. If the ceramics contain a trace amount of impurities (such as manganese and iron), the white reference plates 230 can be discolored by photochemical reactions to cause a deviation in the spectral reflectance in a specific wavelength range.

Figure 9A:
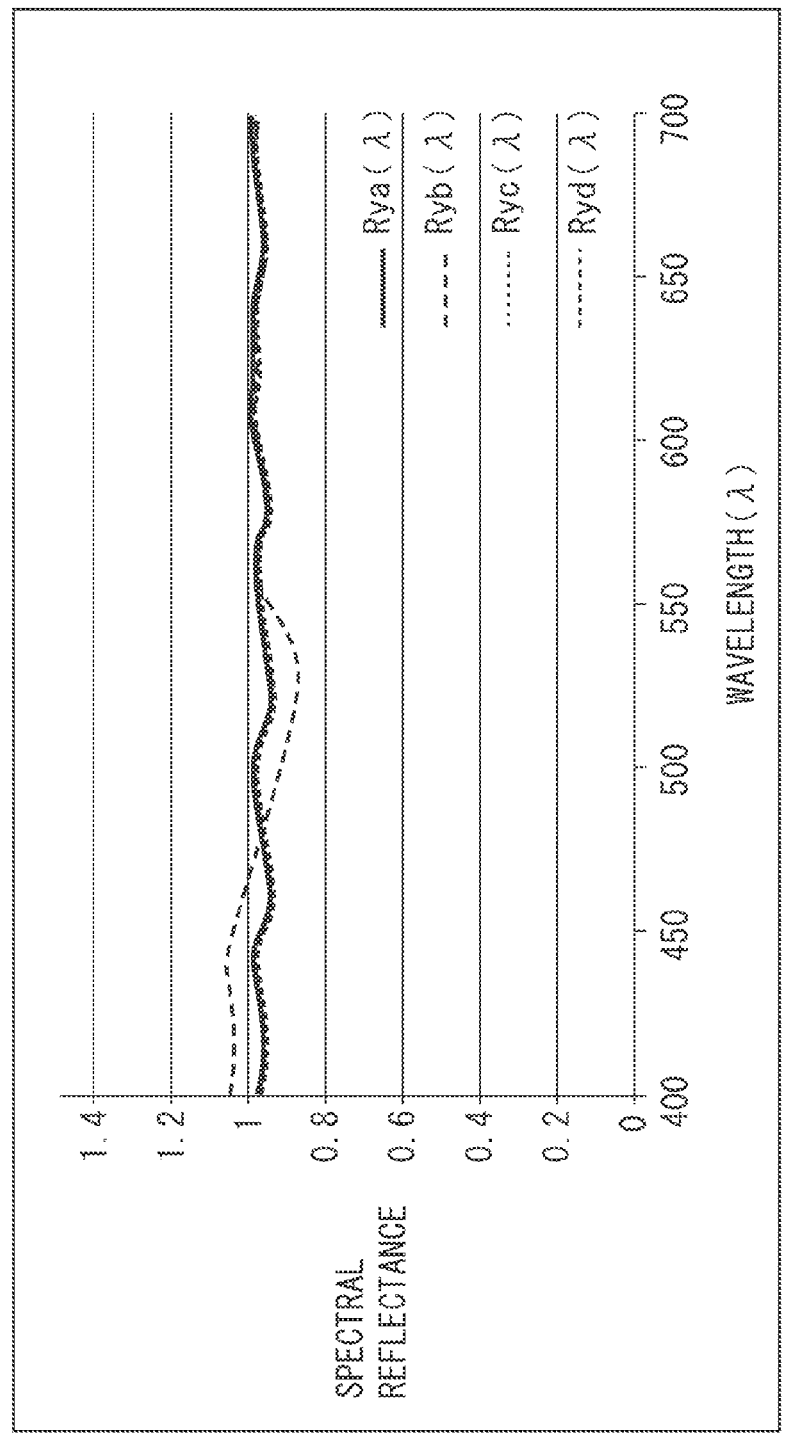
FIG. 9A is a chart illustrating spectral reflectances of color sensors when only a white reference plate 230d is deteriorated.
Figure 10:
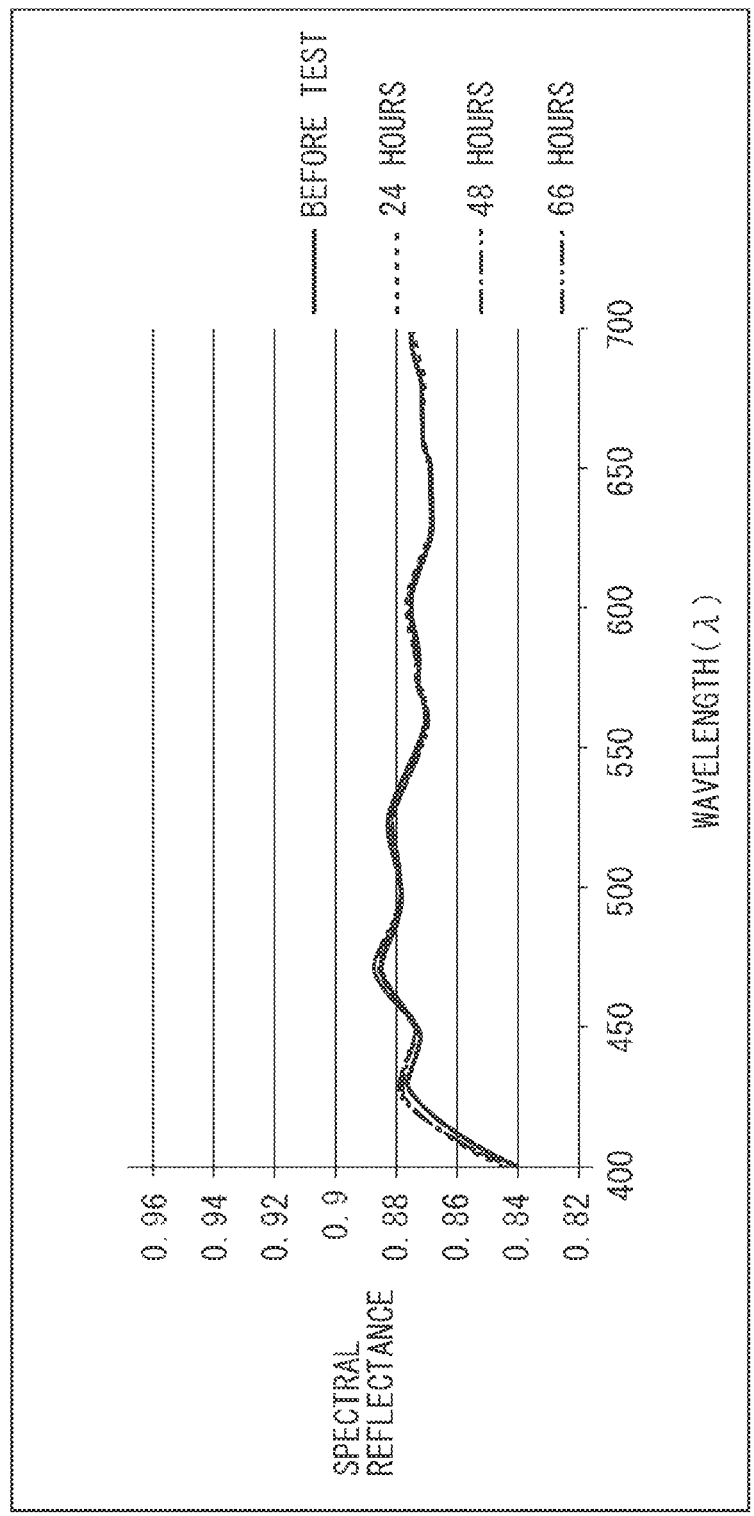
FIG. 10 is a chart illustrating experimental data when a white reference plate 230 is continuously irradiated with light from a white light-emitting diode (LED).

FIG. 9A is a chart illustrating the spectral reflectances Rya(λ) to Ryd(λ) of the color sensors 200a to 200d in a case where only the white reference plate 230d is deteriorated. The chart shows that the spectral reflectance Ryd(λ) of the deteriorated white reference plate 230d deviates in a specific wavelength range. In the present exemplary embodiment, the specific wavelength range employed in step S802 is from 400 nm to 470 nm and from 520 nm to 580 nm. These figures are based on experimental data obtained by continuously irradiating a white reference plate 230 with light from a white LED 201. FIG. 10 illustrates the experimental result.

In FIG. 10, the solid line indicates the initial spectral reflectance of the white reference plate 230. The dotted lines indicate the spectral reflectance of the white reference plate 230 after the white reference plate 230 is continuously irradiated with light from the white LED 201 for certain periods. From the result, it can be seen that as the white reference plate 230 continues being irradiated with the light from the color sensor 200, the spectral reflectance deviates particularly in the ranges of 400 nm to 470 nm and 520 nm to 580 nm. Such deviations of the spectral reflectance cause a tint variation, i.e., deterioration of the white reference plate 230.

If a white reference plate 230 has deteriorated to discolor, the white reference plate 230 needs to be replaced. In step S803, the printer controller 103 displays a massage on the operation unit 180 that a white reference plate 230x accompanying the color sensor 200x needs to be replaced.

In the present exemplary embodiment, the wavelength range for determining deterioration is set to be from 400 nm to 470 nm and from 520 nm to 580 nm. Since such values are determined by the characteristics of the white LEDs 201 and the materials of the white reference plates 230, the wavelength range may be arbitrarily set.

If, in step S802, the spectral reflectance $Ryx(\lambda)$ is determined not to deviate in the specific wavelength range (NO in step S802), the printer controller 103 proceeds to step S804. In step S804, the printer controller 103 determines whether the spectral reflectance $Ryx(\lambda)$ of the color sensor 200x is higher than the average spectral reflectance $Ry\_ave(\lambda)$ across the entire wavelength range. If the spectral reflectance $Ryx(\lambda)$ is higher across the entire wavelength range (YES in step S804), the white reference plate 230 may be considered to be stained.

Figure 9B:
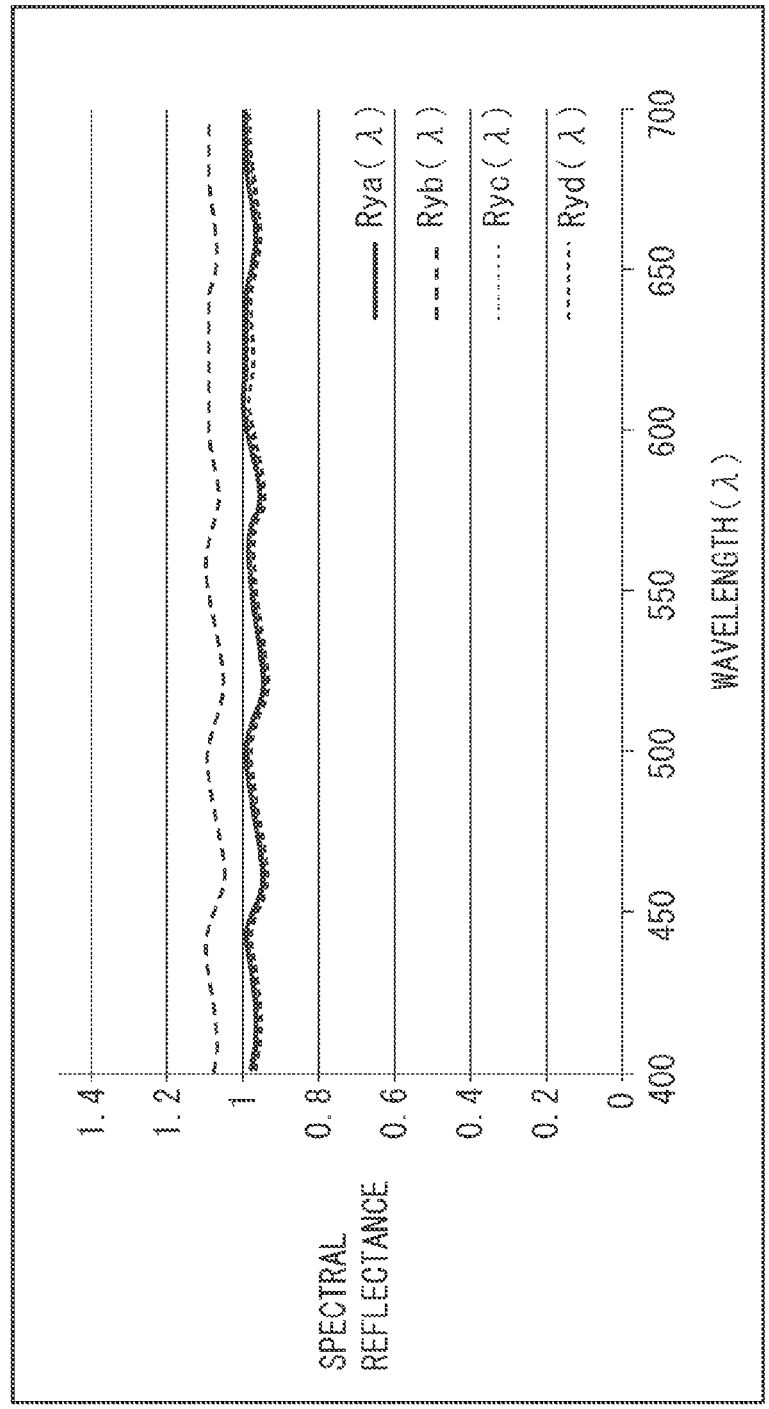
FIG. 9B is a chart illustrating the spectral reflectances of each color sensors when only the white reference plate 230d is stained.

FIG. 9B is a chart illustrating the spectral reflectances $Rya(\lambda)$ to $Ryd(\lambda)$ of the color sensors 200a to 200d when only the white reference plate 230d is stained. The chart shows that if a white reference plate 230 is stained, the spectral reflectance of the reflected light from the white reflectance plate 230 increases across the entire wavelength range. The reason is described below.

When the white reference plate 230x is stained, the irradiation spot of the white LED 230 is partly shaded to reduce the reflected light amount. This reduces the value of $W(\lambda)$ in the foregoing equation (Eq. 1), whereby the calculated spectral reflectance $Ryx(\lambda)$ becomes relatively higher.

A stained white reference plate 230 needs to be cleaned. In step S805, the printer controller 103 displays a message on the operation unit 180 that the white reference plate 230x accompanying the color sensor 200x needs to be cleaned.

If NO in step S804, the color sensor 200x is likely to be defective. In step S806, the printer controller 103 displays a message on the operation unit 180 that the color sensor 200x needs to be replaced.

For example, if the spectral reflectance $Ryx(\lambda)$ of the color sensor 200x is lower than the spectral reflectances of the other color sensors 200 across the entire wavelength range, it can be considered that degradation of the light amount of the white LED 201 may affect the reflectance.

In the foregoing steps S803, S805, and S806, the printer controller 103 gives the user a notification by displaying a message on the operation unit 180. However, the printer controller 103 may issue a notification by using sound or by other methods of display.

As has been described above, according to the present exemplary embodiment, an abnormality of the white reference plates 230 can be determined to prevent a drop in the measurement accuracy of the measurement images (patch images) 220.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2012-131298 filed Jun. 8, 2012, which is hereby incorporated by reference herein in its entirety.

What is claimed is:

1. An image forming apparatus comprising:
   a plurality of white reference plates;
   a plurality of measurement units configured to be arranged in positions opposed to the respective plurality of white reference plates, irradiate the white reference plates with light, and measure reflected light from the white reference plates; and
   a determination unit configured to determine an abnormality of the plurality of white reference plates by using respective measurement results measured by the plurality of measurement units.

2. The image forming apparatus according to claim 1, further comprising:
   an image forming unit configured to form a measurement image on a sheet by using color material; and
   a setting unit configured to set an image forming condition based on measurement results of the measurement image by the plurality of measurement units.

3. The image forming apparatus according to claim 2, further comprising a calculation unit configured to calculate a spectral reflectance of reflected light from a margin portion with respect to each of the plurality of measurement units based on a first measurement value obtained by measuring the margin portion of the sheet on which the measurement image is not formed by the measurement unit and a second measurement value obtained by measuring the white reference plate by the measurement unit,
   wherein the determination unit is configured to determine an abnormality of the white reference plates based on the spectral reflectances of the margin portion with respect to the respective plurality of measurement units calculated by the calculation unit.

4. The image forming apparatus according to claim 3, wherein the determination unit is configured to determine that a white reference plate corresponding to a spectral reflectance that deviates from an average of the respective spectral reflectances among the spectral reflectances of the margin portion with respect to the respective plurality of measurement units in a specific wavelength range is deteriorated.

5. The image forming apparatus according to claim 4, further comprising a notification unit configured to, in response to a determination by the determination unit that any one of the white reference plates is deteriorated, issue a notification to replace the deteriorated white reference plate.

6. The image forming apparatus according to claim 3, wherein the determination unit is configured to determine that a white reference plate corresponding to a spectral reflectance that indicates a value higher than an average of the respective spectral reflectances among the spectral reflectances of the margin portion with respect to the respective plurality of measurement units across an entire wavelength range is stained.

7. The image forming apparatus according to claim 6, further comprising a notification unit configured to, in response to a determination by the determination unit that any one of the white reference plates is stained, issue a notification to clean the stained white reference plate.

8. The image forming apparatus according to claim 2, further comprising a control unit configured to, in a case where the determination unit determines an abnormality of the white reference plates, control the plurality of measurement units not to measure the measurement image, and in a case where the determination unit determines no abnormality of the white reference plates, control the plurality of measurement units to measure the measurement image.

* * * * *